United States Patent [19]

Kunstadter et al.

[11] Patent Number: 5,759,039

[45] Date of Patent: Jun. 2, 1998

[54] METHOD AND SYSTEM FOR APPLYING DESIGNS TO TEETH

[76] Inventors: Maria A. Kunstadter; Michael K. Sigler, both of 2101 Winding Woods Dr., Liberty, Mo. 64068

[21] Appl. No.: 843,989

[22] Filed: Apr. 17, 1997

[51] Int. Cl.⁶ .................. A61C 3/00; A61C 5/00
[52] U.S. Cl. .................. 433/215; 433/229
[58] Field of Search .................. 433/8, 9, 215, 433/229

[56] References Cited

U.S. PATENT DOCUMENTS

| 4,208,795 | 6/1980 | Muhlemann et al. | 433/229 X |
|---|---|---|---|
| 4,439,154 | 3/1984 | Mayclin | 433/229 |
| 4,557,693 | 12/1985 | Elggren | 433/229 |
| 4,797,101 | 1/1989 | Morris | 433/229 |
| 4,820,160 | 4/1989 | Cohen et al. | 433/229 |
| 5,037,301 | 8/1991 | Michnick et al. | 433/229 |
| 5,044,955 | 9/1991 | Jagmin | 433/229 |
| 5,509,805 | 4/1996 | Jagmin | 433/229 X |

*Primary Examiner*—Nicholas D. Lucchesi
*Attorney, Agent, or Firm*—Hovey, Williams, Timmons & Collins

[57] ABSTRACT

A method and system for applying an applique (10) to a person's tooth (16) is disclosed. The applique (10) is formed of fabric or paper material and has a design thereon. Before application, the tooth (16) is cleaned, etched, rinsed, then dried. The selected applique (10) is dipped into a bonding compound (12). The soaked applique (10) is then positioned on the tooth (16), and the bonding compound (12) is cured with a curing light (24). Additional coats of the bonding compound (12) may be applied over the applique (10) and cured to seal the applique from moisture.

16 Claims, 1 Drawing Sheet

METHOD AND SYSTEM FOR APPLYING DESIGNS TO TEETH

BACKGROUND OF THE INVENTION

1. Field of the Invention

The present invention relates to a method and system for applying designs to teeth. More particularly, the invention relates to a method and system for applying appliques having designs printed thereon to teeth.

2. Description of the Prior Art

Many adults and children enjoy adorning themselves with colorful decals or tattoos. Unfortunately, decals do not adhere well to a person's body, and tattoos are somewhat painful and expensive to apply and are not suitable for children. Moreover, tattoos can not be easily removed.

Thus, a need exists for a new method and system for applying designs to a person's body that is more permanent than traditional decals yet does not suffer from the limitations of tattoos.

OBJECTS AND SUMMARY OF THE INVENTION

The present invention solves the above described limitations and provides a distinct advance in the art by providing a method and system for applying semi-permanent yet removable designs to teeth. The designs are printed on paper or fabric appliques sized to fit on the front surface of a person's tooth. A plurality of the appliques may be pre-printed on a single sheet and then individually cut or punched out.

Before application of an applique, the tooth is first cleaned, etched, rinsed, and dried. The selected applique is then dipped into a liquid bonding compound and positioned on the tooth. A curing light is then placed adjacent the tooth and applique to cure the bonding compound. Additional coats of the bonding compound may be applied over the applied applique and cured to seal the applique on the tooth.

An applique applied with the method of the present invention will remain on a tooth for several months without maintenance. However, if the person desires to remove the applique, a dentist can easily do so with conventional dental tools.

The present invention provides numerous advantages. For example, the appliques are more permanent than traditional decals and are less expensive and painful to apply than traditional tattoos. Moreover, the appliques are less obvious than tattoos because they can only be seen when the wearer smiles and are more suitable for children than tattoos.

Another advantage of the present invention is that dentists may decorate their patients' teeth as a part of the patients' regular dental check-ups. The present invention may therefore actually encourage children to visit their dentists more often to have new designs applied to their teeth.

BRIEF DESCRIPTION OF THE DRAWING FIGURES

A preferred embodiment of the present invention is described in detail below with reference to the attached drawing figures, wherein.

DETAILED DESCRIPTION OF THE PREFERRED EMBODIMENTS

Figure 1:
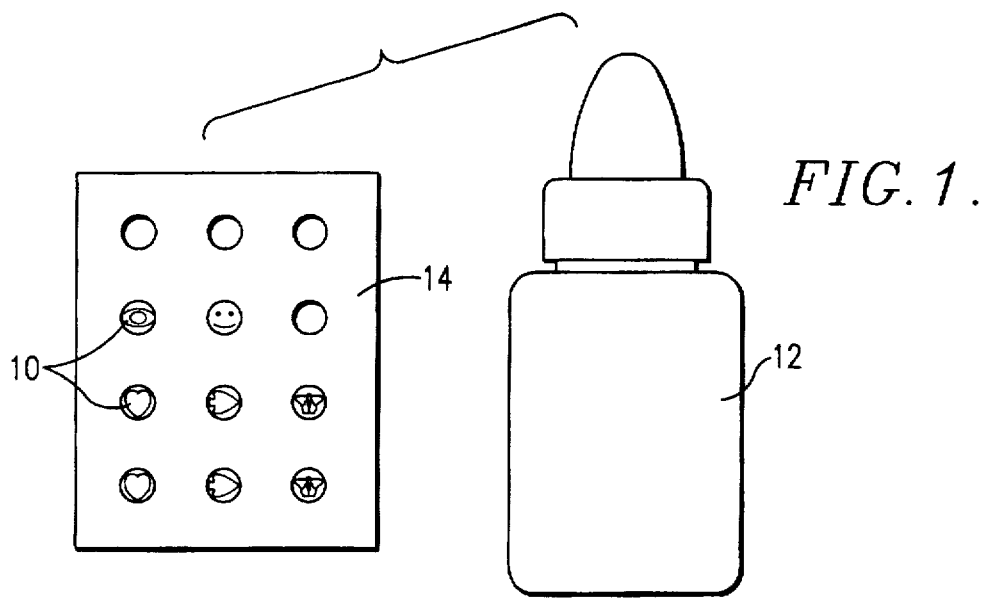
FIG. 1 is a schematic view of a sheet of appliques and a bottle of bonding compound used in the present invention.

The drawing figures illustrate the steps as well as the materials used in the tooth decorating method and system of the present invention. The materials used broadly includes a plurality of appliques 10 and a bonding compound 12 illustrated in FIG. 1.

The appliques 10 are preferably formed of paper or fabric material and each has a design printed thereon. The designs may include hearts, smiley faces, sports logos, etc. A plurality of the appliques 10 are preferably pre-printed on a sheet 14 and individually cut or punched out from the sheet. The individual 10 are preferably cut into individual circular disks each having a diameter of approximately 3–4 millimeters so that the disk fits on the front surface of a tooth.

The bonding compound 12 is preferably an unfilled acrylic resin liquid that sets when activated by light. However, other bonding or adhesive compounds may be used.

Figures 2, 3:
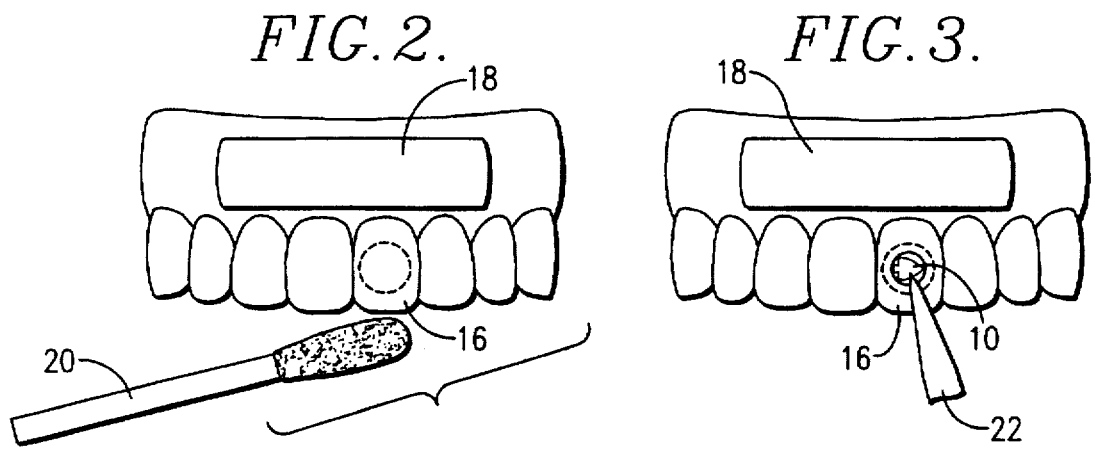
FIG. 2 is a schematic view of a patient's teeth showing a tooth being prepared for receiving an applique.
FIG. 3 is a schematic view showing the application of the applique to the prepared tooth.

To apply an applique 10 to a tooth 16, the tooth is first isolated with a cotton roll 18 as illustrated in FIG. 2. The tooth 16 is then cleaned with pumice or other abrasive using a cotton tipped applicator 20 and etched with a 35% phosphoric acid compound for approximately 10 seconds. The tooth 16 is then rinsed and dried.

The applique 10 selected by the patient is then cut or punched from the sheet 14 and dipped into the bonding compound 12 for approximately 5 seconds. The soaked applique 10 is then placed on the prepared tooth 16 with a dental tool 22 such as a pair of tweezers as illustrated in FIG. 3.

Figures 4, 5:
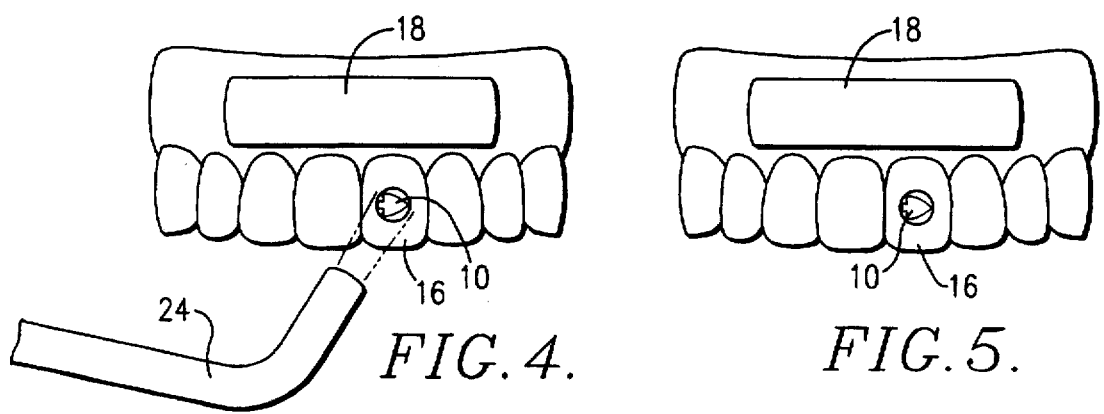
FIG. 4 is a schematic view illustrating the curing of the applied applique.
FIG. 5 is a schematic view illustrating the end result of the invention.

To cure the bonding compound, a light source 24 is placed adjacent the applique 10 for approximately 30 seconds as illustrated in FIG. 4. This securely adheres the applique 10 to the tooth 16. Two additional coats of the bonding compound may be applied over the applique 10 and the surrounding area of the tooth 16 with a brush or scube after the first coat of bonding compound has been thoroughly cured. This seals the applique from moisture and food particles and therefore prolongs the adhesion of the applique to the tooth. The additional coats of bonding compound are also individually cured for approximately 30 seconds with the light source 24.

The method of the present invention results in an applique 10 that is firmly bonded to the tooth 16 as illustrated in FIG. 5. An applique applied in accordance with the present invention will remain on a tooth for several months without maintenance. However, the patient should be advised not to pick at the applique with his/her fingernails. Once the person desires to remove the applique, a dentist can easily do so with conventional dental tools.

Although the invention has been described with reference to the preferred embodiment illustrated in the attached drawing figures, it is noted that equivalents may be employed and substitutions made herein without departing from the scope of the invention as recited in the claims. For example, although the appliques 10 are preferably cut into circular disks, they may be cut into any desired shape without departing from the scope of the present invention.

Having thus described the preferred embodiment of the invention, what is claimed as new and desired to be protected by Letters Patent includes the following:

1. A method of adornment comprising the steps of:

placing an applique formed from a non-metal material and having a design printed thereon on a front surface of one of a person's front teeth so that the applique is visible to others when the person smiles; and bonding the applique on the tooth with bonding material.

2. The method as set forth in claim 1, further including the step of cleaning the tooth with pumice before the applique is placed on the tooth.

3. The method as set forth in claim 2, further including the step of etching the cleaned tooth with a phosphoric acid compound before the applique is placed on the tooth.

4. The method as set forth in claim 1, further including the step of curing the bonding material after the applique has been placed on the tooth.

5. The method as set forth in claim 4, wherein the bonding material is cured by placing a light source adjacent the tooth.

6. The method as set forth in claim 4, further including the step of applying a second coat of bonding material over the applique after it has been placed on the tooth.

7. The method as set forth in claim 6, further including the step of curing the second coat of bonding material.

8. The method as set forth in claim 7, further including the step of applying a third coat of bonding material over the applique after it has been placed on the tooth.

9. The method as set forth in claim 8, further including the step of curing the third coat of bonding material.

10. A method for applying a design to a front surface of one of a person's front teeth so that the design is easily visible to others when the person smiles, said method comprising the steps of:

etching the tooth;

coating an applique formed from a non-metal material and having the design printed thereon with bonding material;

placing the coated applique on the tooth;

curing the bonding material to firmly bond the applique to the tooth; and sealing the applique on the tooth with additional bonding material.

11. A tooth decorating system for decorating teeth, the system comprising:

means for adorning a front surface of one of a person's front teeth, said adorning means including an applique formed from a non-metal material and having a design printed thereon and sized to fit on the front surface of the tooth; and a bonding compound for bonding the applique to the front surface of the tooth.

12. The system as set forth in claim 11, the applique comprising a circular disk having a diameter of approximately 3–4 mm.

13. The system as set forth in claim 11, the non-metal material being selected from the group consisting of paper and fabric.

14. The system as set forth in claim 12, wherein the circular disk is formed of fabric.

15. The system as set forth in claim 11, including a plurality of the appliques formed in a sheet.

16. The system as set forth in claim 11, wherein the bonding formula comprises a light activatable, unfilled acrylic resin liquid.

* * * * *